(12) United States Patent
Stephan

(10) Patent No.: US 10,632,284 B2
(45) Date of Patent: Apr. 28, 2020

(54) CATHETER PORT

(71) Applicant: Rabie Stephan, Amherst, NY (US)

(72) Inventor: Rabie Stephan, Amherst, NY (US)

( * ) Notice: Subject to any disclaimer, the term of this patent is extended or adjusted under 35 U.S.C. 154(b) by 1244 days.

(21) Appl. No.: 14/874,172

(22) Filed: Oct. 2, 2015

(65) Prior Publication Data

US 2017/0095644 A1 Apr. 6, 2017

(51) Int. Cl.
*A61M 25/01* (2006.01)
*A61M 39/02* (2006.01)
*A61M 25/02* (2006.01)

(52) U.S. Cl.
CPC ..... *A61M 25/0111* (2013.01); *A61M 39/0247* (2013.01); *A61M 2025/0266* (2013.01); *A61M 2039/027* (2013.01); *A61M 2039/0258* (2013.01); *A61M 2039/0273* (2013.01)

(58) Field of Classification Search
CPC .............. A61M 25/0111; A61M 25/02; A61M 2039/0273; A61M 2039/0261; A61M 2039/0288; A61M 2039/027; A61M 2039/025; A61M 2039/0252; A61M 2039/0232; A61M 2039/0285; A61M 2039/0264; A61M 2039/0276; A61M 2025/028; A61M 29/0247
See application file for complete search history.

(56) References Cited

U.S. PATENT DOCUMENTS

| | | | |
|---|---|---|---|
| 4,210,148 A * | 7/1980 | Stivala | A61B 17/0466 606/232 |
| 4,834,068 A * | 5/1989 | Gottesman | A61B 1/00142 128/846 |
| 5,234,411 A * | 8/1993 | Vaillancourt | A61M 25/0111 604/158 |
| 5,368,574 A | 11/1994 | Antonacci | |
| 5,405,334 A | 4/1995 | Roth | |
| 5,562,618 A | 10/1996 | Cai et al. | |
| 5,807,341 A * | 9/1998 | Heim | A61M 25/02 604/174 |
| 5,817,072 A | 10/1998 | Lampropoulos et al. | |
| 5,882,341 A | 3/1999 | Bousquet | |
| 6,228,063 B1 * | 5/2001 | Aboul-Hosn | A61B 17/3423 604/174 |
| 6,872,198 B1 | 3/2005 | Wilson | |
| 7,794,431 B2 | 9/2010 | Porter et al. | |

(Continued)

*Primary Examiner* — Nathan R Price
*Assistant Examiner* — Weng Lee
(74) *Attorney, Agent, or Firm* — Tracy Jong Law Firm; Tracy P. Jong; Cheng Ning Jong

(57) ABSTRACT

A catheter port adapted to be selectively secured topically to a patient's body about a site at which a catheter is to be inserted into the patient's body. The catheter port includes a cushion adapted to be secured to the patient's epidermis at its bottom surface about the site and at its top surface to a member, an inner tube having one portion mounted on the member and having another portion that is adapted to extend into the patient's body about the site for guiding movement of a catheter relative to the site and for preventing any portion of the catheter from ever contacting the patient's epidermis, an outer tube having a proximal end mounted on one of the member and inner tube, an intermediate portion extending away from the one of the member and the inner tube in a distal end and a septum mounted on the outer tube.

11 Claims, 11 Drawing Sheets

(56) References Cited

U.S. PATENT DOCUMENTS

| | | |
|---|---|---|
| 8,267,915 B2 | 9/2012 | Daly |
| 8,795,161 B2 * | 8/2014 | Carter ................ A61B 17/3423 |
| | | 600/184 |
| 2002/0019610 A1 * | 2/2002 | Bousquet .............. A61M 1/285 |
| | | 604/175 |
| 2002/0165494 A1 * | 11/2002 | Bierman ............... A61M 25/02 |
| | | 604/174 |
| 2005/0119637 A1 * | 6/2005 | Lundgren ......... A61M 39/0247 |
| | | 604/539 |
| 2005/0288622 A1 * | 12/2005 | Albrecht ............ A61B 17/3417 |
| | | 604/23 |
| 2007/0055205 A1 * | 3/2007 | Wright .................. A61F 13/023 |
| | | 604/174 |
| 2007/0149949 A1 | 6/2007 | Porter et al. |
| 2007/0282271 A1 | 12/2007 | Kaplan et al. |
| 2008/0114308 A1 | 5/2008 | Di Palma |
| 2009/0205643 A1 * | 8/2009 | Tanaka ................... A61K 9/007 |
| | | 128/200.24 |
| 2011/0218392 A1 * | 9/2011 | Honaryar .......... A61M 39/0208 |
| | | 600/37 |
| 2012/0041377 A1 | 2/2012 | Haak |
| 2012/0232489 A1 | 9/2012 | Helm, Jr. |
| 2013/0178708 A1 * | 7/2013 | Malkowski ........ A61B 17/0293 |
| | | 600/204 |
| 2014/0207086 A1 | 7/2014 | Stats |
| 2014/0249375 A1 * | 9/2014 | Rodrigues, Jr. ... A61M 39/0247 |
| | | 600/227 |

\* cited by examiner

CATHETER PORT

BACKGROUND OF THE INVENTION

1. The Field of the Invention

The present invention is directed generally to a catheter port. More specifically, the present invention is directed to a catheter port adapted to facilitate the use of a catheter on a patient and isolate the catheter from the patient's skin.

2. Background Art

Numerous solutions have been attempted in combating infections caused by intravascularly implanted medical devices or catheters. The treatment of entry sites of percutaneously implanted devices have dramatically reduced infections caused by the transfer of microbes from the surface tissue or skin of a person or animal to the intravascular, organ or body tissues. However, infections due to microbes already present within the body remain serious cause of infections and ill health. Common solutions include, but not limited to, coating of surfaces with anti-microbial drugs, modification of surface charges, implementation of ultrasonic vibrating devices, etc. However, such solutions may cause negative side effects such as in the case of anti-microbial drugs. Modification of surface charges and implementation of ultrasonic vibrating devices require complicated equipment which not only increase costs but also require constant or periodic power use, sophisticated control and actuating devices.

Catheter entry sites are fertile grounds for infectious agents, e.g., bacteria, fungi and viruses to be introduced into a patient's body by direct contact of catheters with unclean site surfaces, such as, the skin layer and percutaneous tissue. As a catheter is inserted into a patient's body, any infectious agents garnered from such surfaces can be drawn into the body quite readily. The Applicant discovered that a major source of infection is derived from the patient's skin layer and percutaneous tissue. By isolating such surfaces from the catheters, such infectious agents can be blocked from entering the patient's body. None of the references below discloses a catheter apparatus or device capable of preventing intrusion of infectious agents through catheter entry sites.

U.S. Pat. No. 5,817,072 to Lampropoulos et al. (hereinafter Lampropoulos) discloses an indwelling catheter apparatus for providing fluid to the central venous system. The indwelling catheter apparatus includes an indwelling cannula adapted for insertion into subcutaneous tissue in the chest wall and approximately within the superior vena cava, the indwelling cannula having an indwelling distal end, the distal end having an exit port in fluid communication with the superior vena cava; a proximal hub end adapted for positioning outside of the body; and a primary lumen for delivering fluid to the circulatory system; and delivery means for delivering fluid medicament to the subcutaneous tissue surrounding a portion of the cannula. Lampropoulos fails to disclose a mechanism for preventing intrusion of infectious agents through the punctured site through which the indwelling catheter apparatus is administered. Upon administering the apparatus, the Lampropoulos apparatus lacks a physical barrier that prevents infectious agents from being drawn into or from entering the punctured site. As the cylindrical wall (36 of Lampropoulos) is not secured against the skin layer or subcutaneous tissue, the catheter device (12 of Lampropoulos) is free to move with respect to such body parts. Lampropoulos also lacks a means for cushioning the catheter device (12 of Lampropoulos) against the surface upon which it is attached.

U.S. Pat. Pub. No. 20070282271 to Kaplan et al. (hereinafter Kaplan) discloses a device for protecting the proximal extension of an indwelling catheter and its percutaneous puncture site from moisture, fluids and risk of infection and maintains a clean environment and a fluid-impermeable and bacteria growth-inhibiting seal against the patient's skin when bathing, showering or swimming, and also protecting others from being exposed to the patient's blood and catheter at that time. A faceplate is adhered to the skin about the catheter exit site with medical adhesive, the proximal end of the catheter is secured to the faceplate to prevent it from moving from within the patient's body, and a water-impermeable housing is sealed to the faceplate, with the proximal end of the catheter extending into a cavity of the housing. An antimicrobial material may be disposed on the backside of the faceplate. The device allows a patient to shower, bathe and swim while preventing the catheter from being dislodged from the patient. Kaplan fails to disclose a mechanism for preventing intrusion of infectious agents through the catheter exit. Catheters can come in contact with the skin layer and subcutaneous tissue as the faceplate does not prevent such contact.

Thus, there is a need for a catheter port capable of isolating a catheter from contacting a patient's skin when the catheter is being administered to the patient or when the catheter is left in place upon its administration.

SUMMARY OF THE INVENTION

In accordance with the present invention, there is provided a catheter port adapted to be selectively secured topically to a patient's body about a site at which a catheter is to be inserted into the patient's body. The catheter port includes a cushion having a bottom surface adapted to be secured to the patient's epidermis about the site and a top surface attached to a first surface of a member, an inner tube having one portion mounted on the member and having another portion that is adapted to extend into the patient's body about the site for guiding movement of a catheter relative to the site and for preventing any portion of the catheter from ever contacting the patient's epidermis, an outer tube having a proximal end mounted on either the member or the inner tube, an intermediate portion extending away from either the member or the inner tube in a distal end and a septum mounted on the outer tube.

In one embodiment, one portion of the cushion is provided with an adhesive coating that is adapted to secure the cushion to the patent's epidermis.

In one embodiment, at least one of an antibiotic substance and an anti-microbial substance is applied between a portion of the cushion and the patient's epidermis to provide a sterile field about the site.

In one embodiment, at least a portion of the cushion is impregnated with an antibiotic substance. In another embodiment, at least a portion of the cushion is impregnated with an anti-microbial substance. In one embodiment, the cushion is formed of a foam material.

In one embodiment, the septum is mounted on a marginal portion of the outer tube adjacent the distal end.

In one embodiment, the septum includes a plurality of slits radiating outwardly from a common point.

In one embodiment, the outer tube distal end is arranged to be flexed relative to the outer tube proximal end.

In one embodiment, the outer tube intermediate portion has a bellows portion to accommodate flexing, the outer tube intermediate portion is disposed between the outer tube distal end and the outer tube proximal end. In another embodiment, the outer tube intermediate portion has a thin wall portion to accommodate flexing.

In one embodiment, the septum is arranged to create a gap between the outer tube and the catheter such that the catheter is prevented from contacting engagement with the outer tube.

An object of the present invention is to provide a catheter port capable of isolating a catheter from contacting a patient's skin when the catheter is being administered to the patient or when the catheter is left in place upon its administration.

An object of the present invention is to provide a catheter port capable of being secured to the skin of a patient without fear of unintended detachment due to normal activities surrounding administration and maintenance of the catheter port.

An object of the present invention is to provide a catheter port capable of being administered without causing a significant amount of additional cost and labor over conventional catheter administering practices.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST 2, 2A, 2B, 2C, 2D, 2E—catheter port
4—member
6—inner tube
8—flexible portion—bellow or pliable material
10—outer tube
12—septum
14—pin
16—catheter
18—tip of catheter
20—sleeve adapter
22—sleeve assembly
24—slot
26—direction in which thin wall portion bends
28—cushion
30—slits
32—thin wall portion
34—skin surface
36—skin layer
38—outer diameter of inner tube
40—outer diameter of member
42—outer diameter of cushion
44—thickness of member
46—thickness of cushion
48—inner diameter of outer tube
50—outer diameter of outer tube
52—length of inner tube
54—collar
56—height of collar
58—height of outer tube
60—inner diameter of inner tube
62—sleeve
64—distal end of sleeve
66—proximal end of sleeve
68—spacer
70—support block
72—patient
74—needle
76—puncture site
78—syringe
80—physician's hand
82—guidewire
84—guidewire cover
86—right shoulder
88—channel
90—needle tip

PARTICULAR ADVANTAGES OF THE INVENTION

The present catheter port eliminates any contact of catheters with skin, thereby eliminating any transmission of diseases to a patient due to skin-catheter contact. Without the present catheter port, any initial introduction or re-introduction of a catheter causes contamination of the segments of the catheter coming into contact with the skin. Any parts of a catheter that have come in contact with the skin can no longer be considered sterile despite present day attempts to create or re-create a sterile field on the skin surface with antimicrobial or antibiotic substances. The present catheter prevents any such contact from occurring.

As a catheter port provides isolation of the patient's epidermis with the insertion site of the patient, a catheter replacement can be performed in a sterile manner as an soiled catheter can be simply pulled out with the catheter port left intact at the insertion site and a new catheter inserted without coming into contact with the patient's epidermis. During the replacement of an old catheter with an unsoiled one, the epidermis surrounding the insertion site is most likely no longer sterile. By removing the possibility of any contact with the epidermis, an unsoiled catheter can be kept sterile during its insertion in the patient's body.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 1:
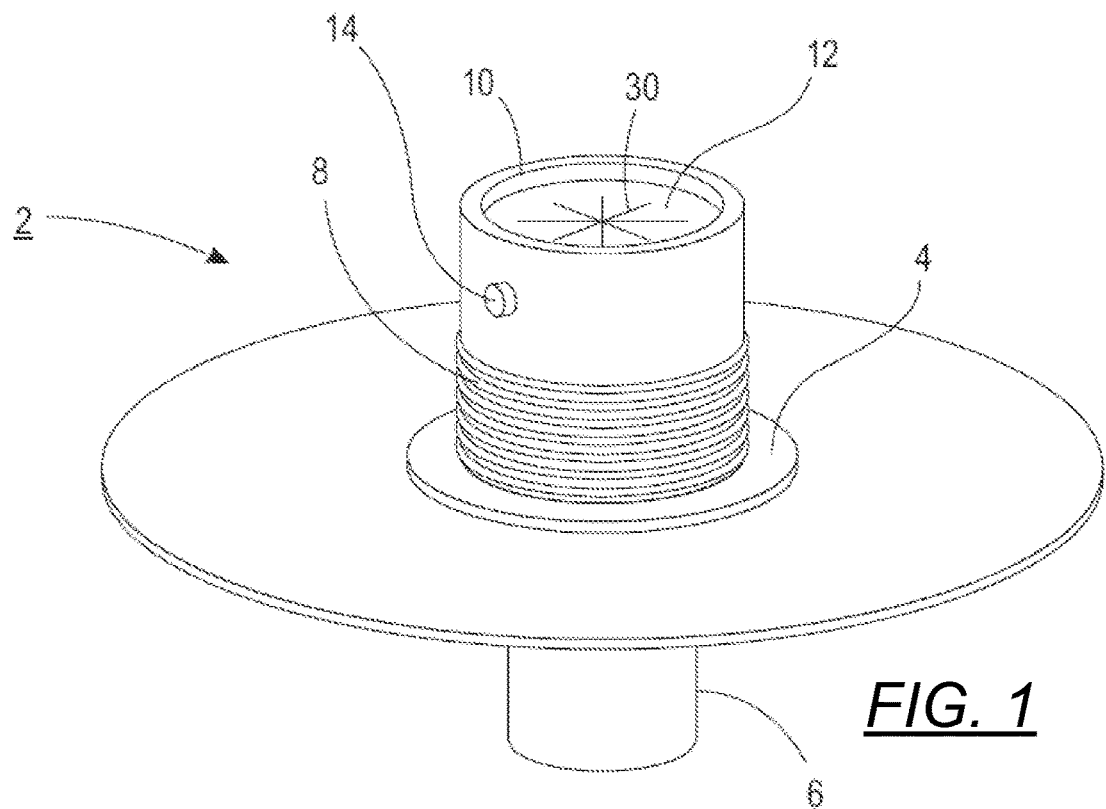
FIG. 1 is a top perspective view of one embodiment of a catheter port.
Figure 2:
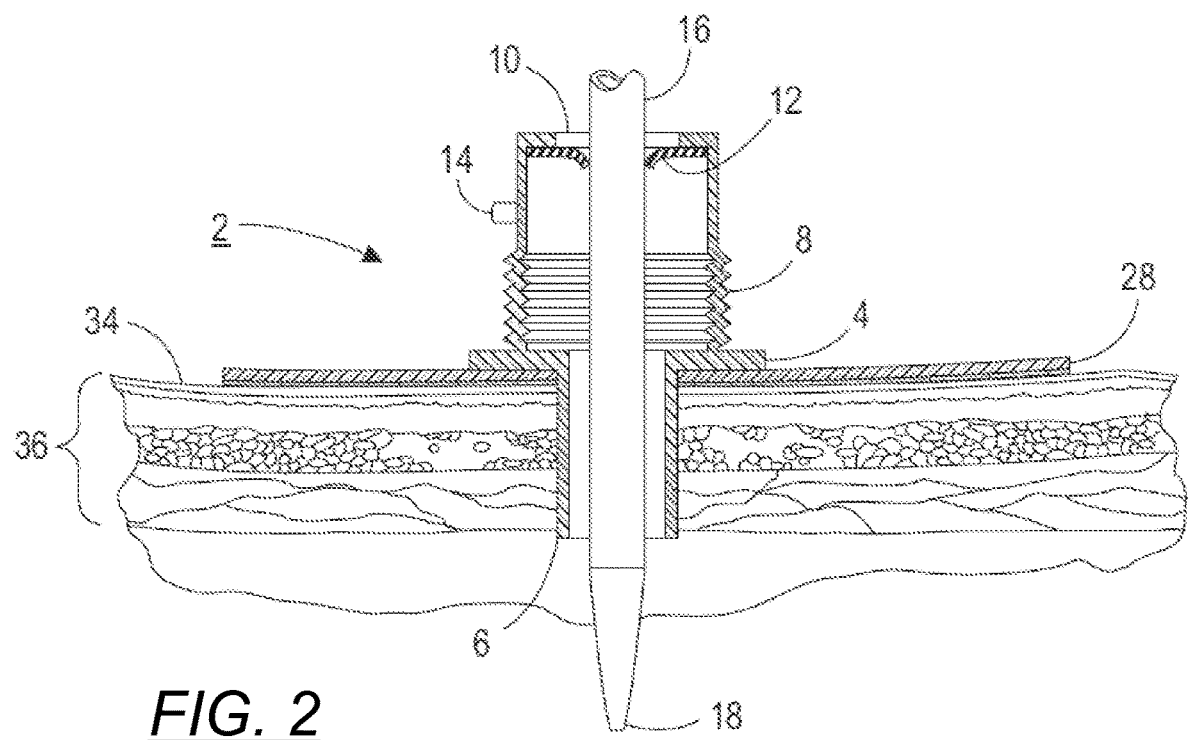
FIG. 2 is a cross-sectional view depicting a catheter port adapted to a catheter that is being inserted into human tissue.

FIG. 1 is a top perspective view of one embodiment of a catheter port 2. FIG. 2 is a cross-sectional view depicting a catheter port 2 adapted to a catheter 16 that is being inserted into human tissue. The catheter port 2 is secured topically to a patient's body, e.g., via human skin layer 36, about a site at which a catheter 16 is to be inserted into the patient's body. At its basic form, the catheter port 2 includes a cushion 28 attached to a member 4 and an inner tube 6. The member 4 is essentially a flange serving as a platform to which a cushion 28 is attached in addition to adding rigidity to the catheter port 2. The member 4 includes an aperture through which a catheter 16 is to be inserted. The inner tube 6 includes one portion mounted on the member and another portion that is adapted to extend into the patient's body about the site for guiding movement of a catheter 16 relative to the site and for preventing any portion of the catheter from ever contacting the patient's epidermis. In one embodiment, the inner tube 6 is a cylindrical tube. In another embodiment, the inner tube is a frustoconical tube having a narrowing free end to make its insertion into a patient's body easier. In one embodiment, the inner tube 6 includes a smooth outer surface. In another embodiment, the inner tube 6 includes a ribbed surface to aid in preventing disengagement of the catheter port 2 from a patient's body. In one embodiment, the member 4 is a substantially circularly shaped flange.

In one embodiment, the catheter port 2 further includes an outer tube 10 and a septum 12. The outer tube 10 includes a proximal end, an intermediate portion and a distal end. The outer tube 10 is configured to be mounted to the member 4 at the proximal end and the intermediate portion is configured to extend away from the member 4 to the distal end. The septum 12 is mounted on the distal end of the outer tube 10 where it is arranged to create a gap between the outer tube 10 and the catheter 16 such that the catheter 16 is prevented from contacting engagement with the outer tube 10, further centering the catheter 16 within the inner tube 6, reducing any tendencies of the catheter 16 to be pressed against a corner of the catheter port 2. In the embodiment shown, the septum 12 includes a plurality of slits 30 radiating outwardly from a common point. In another embodiment, the septum includes a plate having an aperture to allow penetration of the catheter. The outer tube 10 distal end is arranged to be flexed relative to the outer tube 10 proximal end, facilitating any maneuvers that may be required of a catheter during use. The intermediate portion includes a flexible portion, constructed, e.g., from bellows portion 8 to accommodate such flexing, where the intermediate portion is disposed between the outer tube 10 distal end and the outer tube 10 proximal end.

The site at which a catheter is to be inserted can be rather uneven due to the patient's skin contours or anatomical variations at the site. Therefore, a flat-faceted material may not be comfortably and sealingly disposed over such site. In one embodiment, a cushion 28 is configured to be disposed between the patient's epidermis about the site and the first surface of member 4 to accommodate differences in the distance between the patient's epidermis and the first surface of member 4. In this embodiment, the first surface of the member 4 is adhered or otherwise attached to a top surface of the cushion 28. In one embodiment, the cushion 28 is attached to the member 4 by an adhesive. In another embodiment, the cushion 28 is integrally built with the member 4 or fused to the member 4 via common welding techniques. In another embodiment, the cushion 28 is co-formed with the member 4 from a material, e.g., polyurethane, such that no welding or adhesives will be necessary to attach the cushion 28 to the member 4. An adhesive coating is provided to the bottom surface of the cushion 28 such that the cushion 28 may be secured to the patent's epidermis.

The cushion 28 is essentially a pliable disc with a hollowed center such that the inner tube 6 of a catheter port may be inserted through it. The cushion 28 is preferably constructed from a non-allergenic and malleable material (e.g., foam, etc.) suitable to conform to a patient's body structure at the application site of the catheter port 2. In one embodiment, at least a portion of the cushion 28 is impregnated with an anti-microbial substance to prevent, inhibit, or kill undesirable or harmful microbes. The presence of the antimicrobial substance can prevent or eliminate contamination of the surface of the equipment coming into contact with an undesirable or harmful microbe. In another embodiment, the cushion 28 is impregnated with an antibiotic substance.

In one embodiment, an antibiotic substance or an antimicrobial substance is applied where such substance acts between the patient-facing surface of the member 4 and the patient's epidermis 34 to provide a sterile field about the site.

Figure 3:
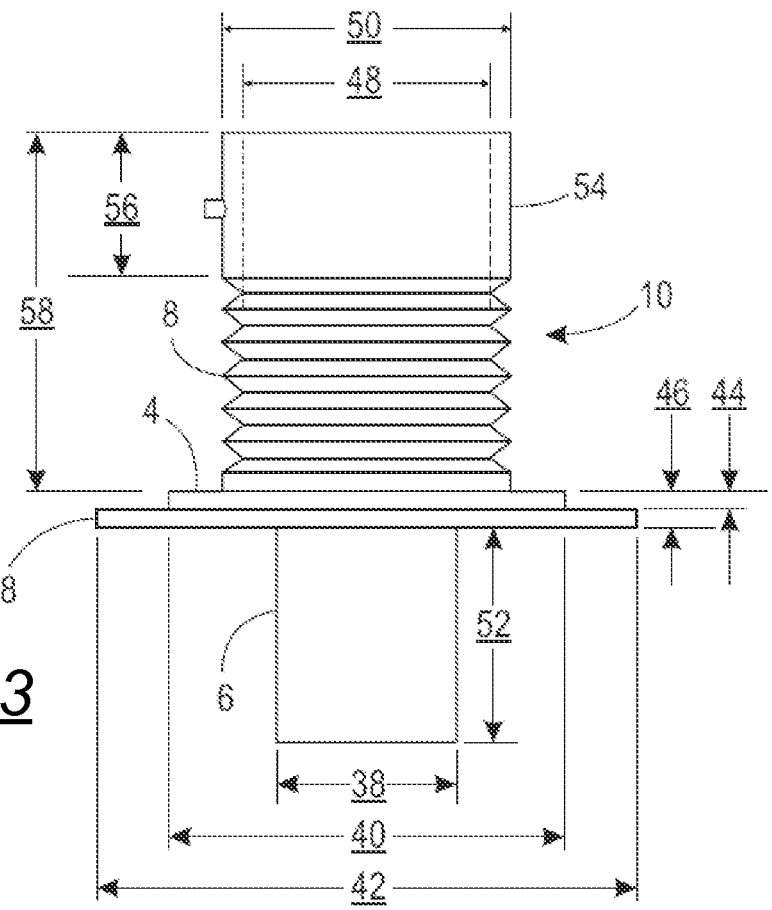
FIG. 3 is a side view of one embodiment of a catheter port, depicting exemplary dimensions of the catheter port.
Figure 4:
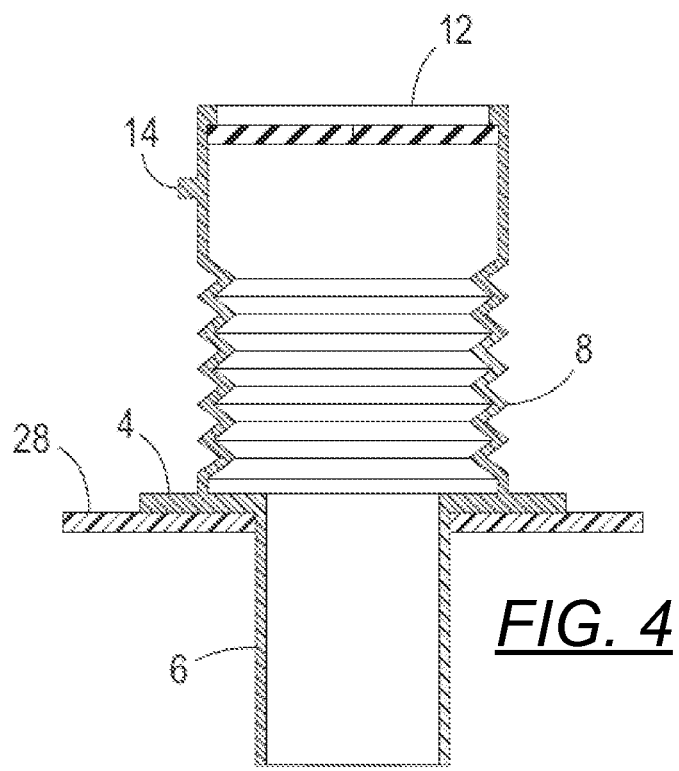
FIG. 4 is a side cross-sectional view of one embodiment of a catheter port.
Figure 5:
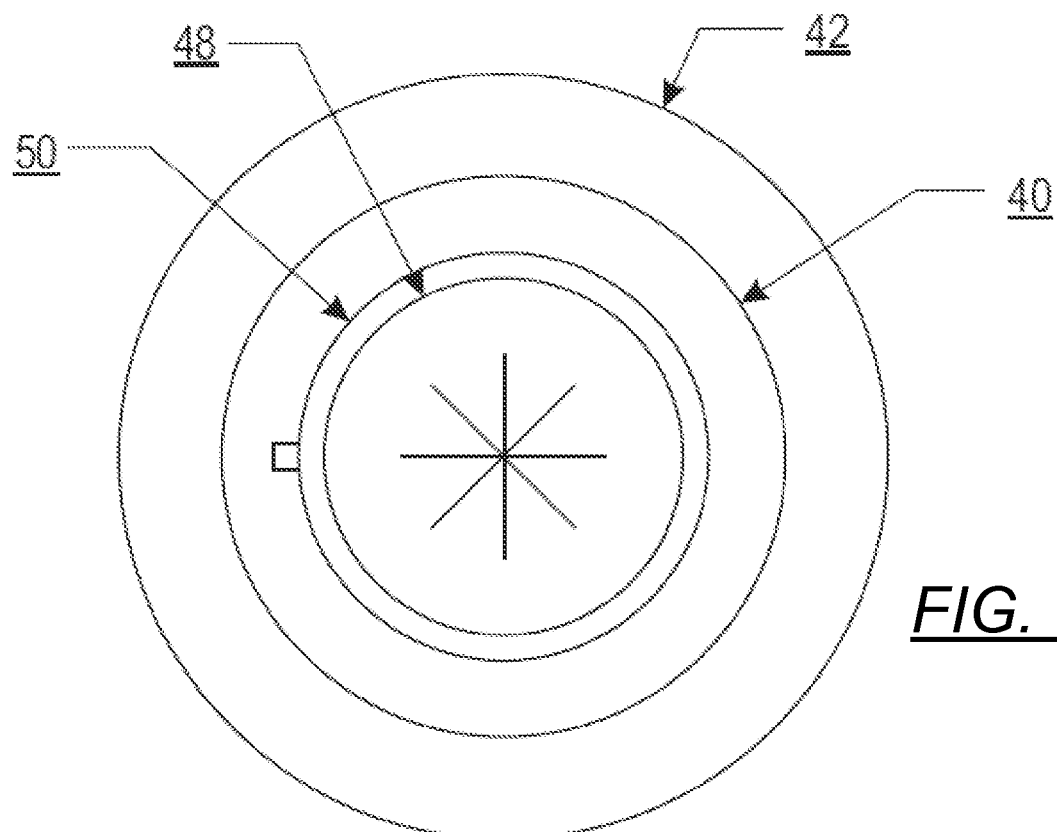
FIG. 5 is a top view of one embodiment of a catheter port.
Figure 6:
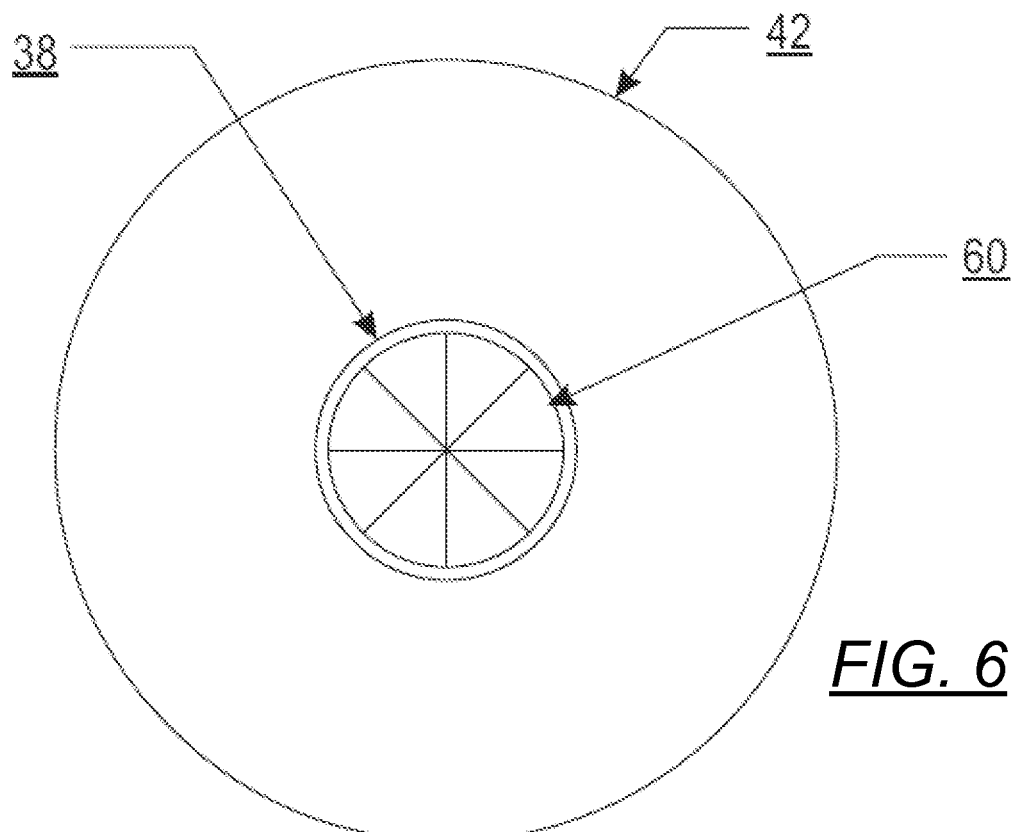
FIG. 6 is a bottom view of one embodiment of a catheter port.

FIG. 3 is a side view of one embodiment of a catheter port 2, depicting exemplary dimensions of the catheter port. FIG. 4 is a side cross-sectional view of one embodiment of a catheter port. FIG. 5 is a top view of one embodiment of a catheter port 2. FIG. 6 is a bottom view of one embodiment of a catheter port 2. The cushions 28 are preferably configured significantly more prominently in diameter than the member 4 to provide sufficient cushioning of the catheter port 2 against the patient's skin 34 surface and to provide sufficient attachment surface area to reduce the likelihood of accidental detachment of the catheter port 2 from the patient while in use. The outer diameter 40 of the member 4 ranges from about 1 to about 2 cm. The outer diameter 42 of the cushion 28 ranges from about 2.5 cm to about 4.5 cm. The outer diameter 38 of inner tube ranges from about 4.5 mm to about 5 mm. The thickness 44 of the member 4 is about 2 mm. The thickness 46 of the cushion 28 is about 1 mm. The wall thickness 48 of the outer tube 10 is about 0.5 mm. The outer diameter 50 of the outer tube 10 is about 1 cm. The length 52 of inner tube 6 ranges from about 1 cm to about 3 cm. The outer tube 10 includes a collar 54. The height 56 of collar 54 is about 1.5 cm. The height 58 of outer tube 10 ranges from about 1 cm to about 2 cm. The wall thickness of the inner tube 6 is about 1 mm.

Figure 7:
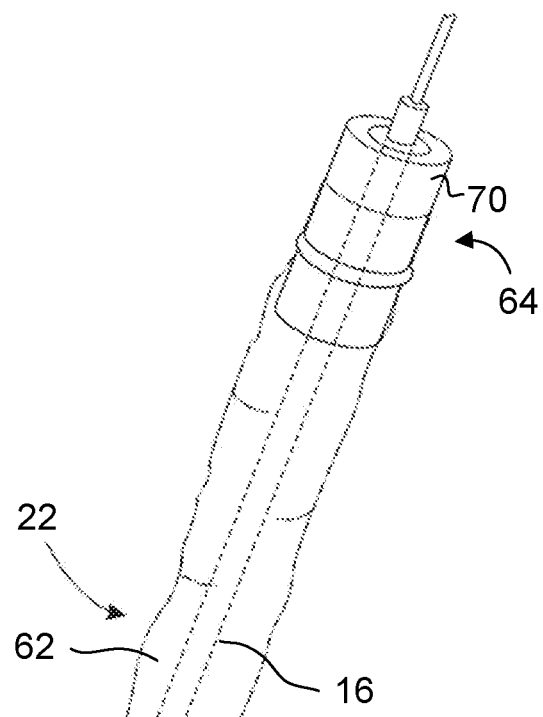
FIG. 7 is a top perspective view of one embodiment of a catheter port adapted to a sleeve assembly.
Figure 7:
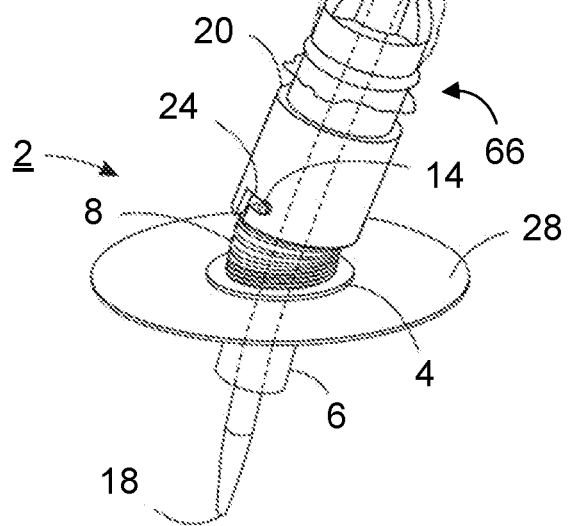

FIG. 7 is a top perspective view of one embodiment of a catheter port adapted to a sleeve assembly 22. Although the catheter port can be used without a sleeve assembly, when combined with the catheter port 2, the sleeve assembly 22 extends the length of the catheter port 2, increasing the amount of grasp points on the catheter port 2, facilitating the handling of the catheter port 2 relative to the catheter 16 and reducing the possibility of cross-contamination by protecting a larger area of the outer surfaces of the catheter. The sleeve assembly 22 has a proximal end 66 and a distal end 64. The sleeve assembly 22 includes a sleeve adapter 20 disposed on the proximal end 66 of the sleeve assembly 22, a support block 70 disposed on the distal end 64 of the sleeve assembly 22 and a sleeve 62 interposed between the proximal end 66 of the sleeve assembly 22 and the distal end 64 of the sleeve assembly 22. In use, the sleeve adapter 20 is configured to be capable of connection to the distal end of the outer tube 10. In one embodiment, the sleeve adapter 20 is equipped with a Bayonet Navy Connector (BNC) style connector which includes a slot 24. The slot 24 is configured to be coupled to a pin 14 disposed on the collar 54. In securing the sleeve assembly 22 to the catheter port 2, the sleeve adapter 20 is first brought close to the collar 54 such that they are roughly aligned and the opening of the slot 24 is aligned with the pin 14. The sleeve adapter 20 is advanced toward and over the outer tube 10 while continuing to be rotated until the pin 14 finally seats and is spring detented at the closed end of slot 24. Upon installation of the sleeve assembly 22, a catheter 16 may be inserted through the support block 70, sleeve 62 and sleeve adapter 20 into the catheter port 2. In operating environments where it is difficult to avoid contact of a catheter with the environment just outside of the surgical site, the sleeve assembly 22 reduces the amount of such contact while providing more grasping points for the surgical professionals so that no direct contact of the surgical professionals with the catheter 16 is necessary.

Figure 8:
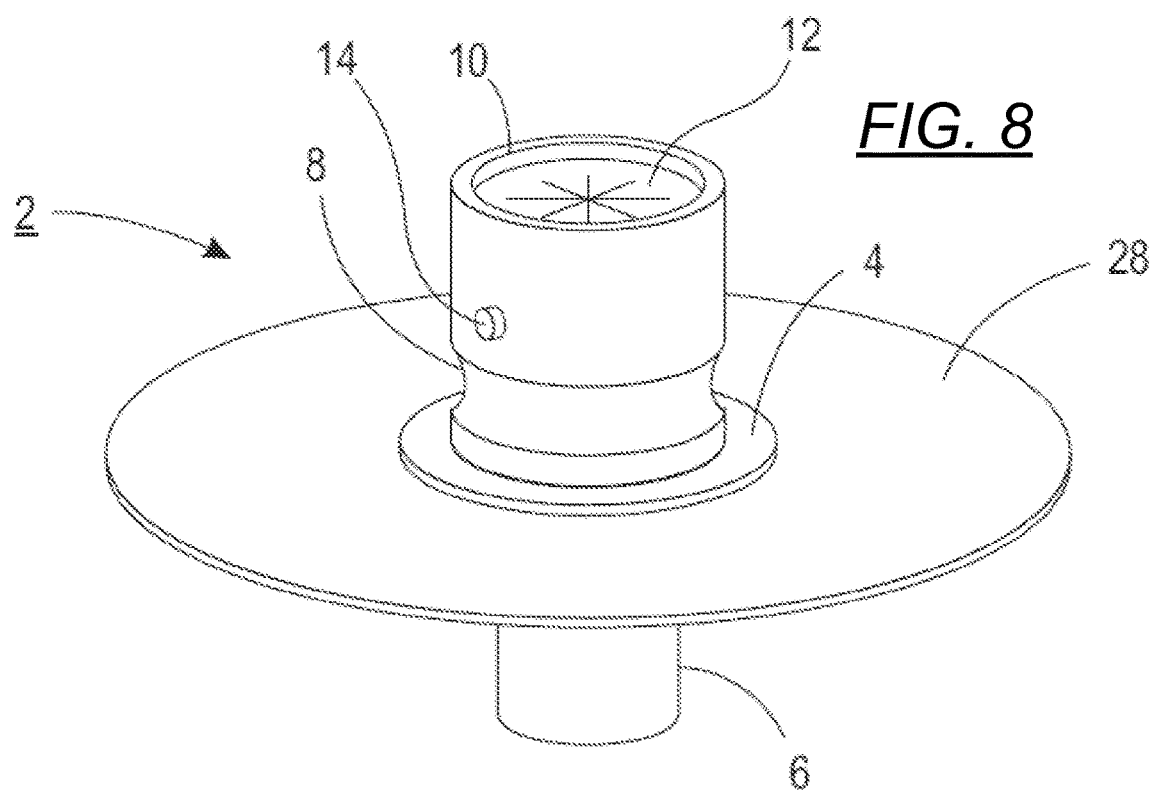
FIG. 8 is a top perspective view of another embodiment of a catheter port.
Figure 9:
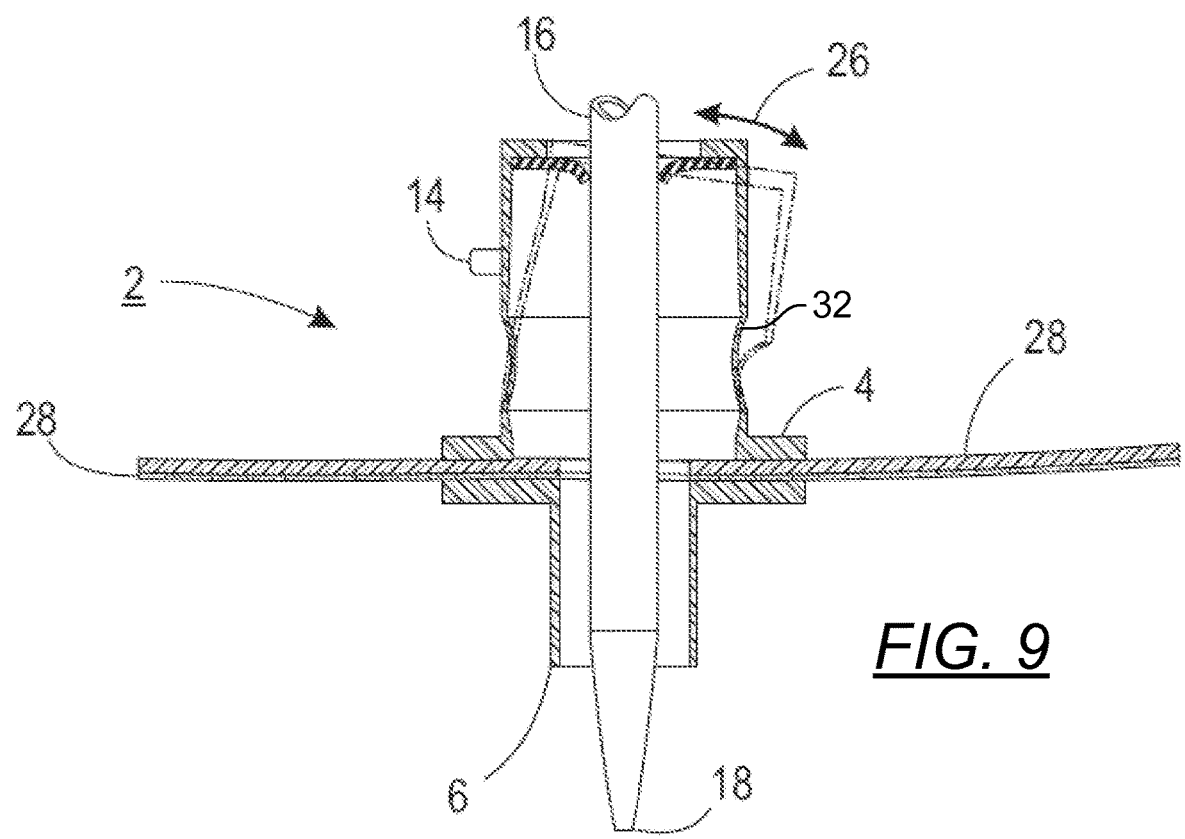
FIG. 9 is a cross-sectional view of a catheter port adapted to a catheter.

FIG. 8 is a top perspective view of another embodiment of a catheter port. FIG. 9 is a cross-sectional view of a catheter port adapted to a catheter. In this embodiment, the intermediate portion 8 includes a thin wall portion 32 to accommodate flexing. Again, the intermediate portion is disposed between the outer tube distal end and the outer tube proximal end. It shall be noted when a force is applied to the outer tube, e.g., when catheter is pulled against the septum, the outer tube bends in direction 26, accommodating such applied force while ensuring that the catheter 16 is still set a distance from the inner surfaces of the outer tube to keep such surfaces clean.

Figure 10:
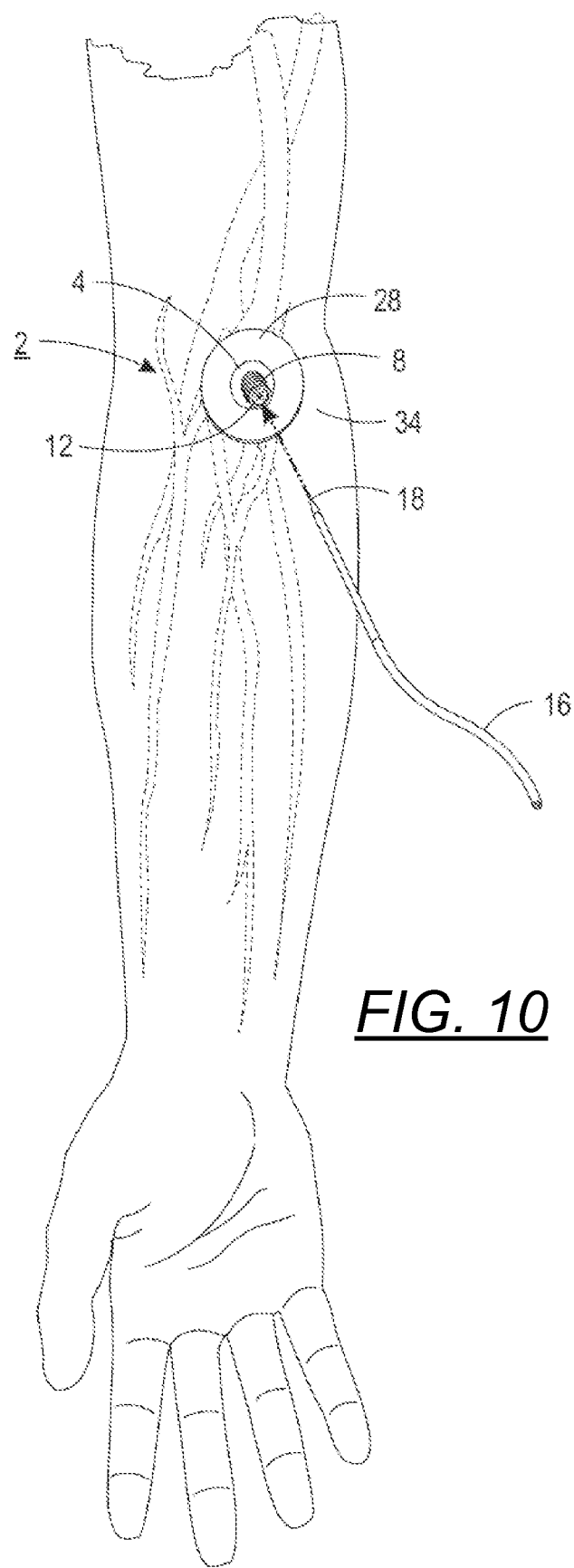
FIG. 10 is a diagram depicting exemplary locations where catheter ports may be used on a human.
Figure 11:
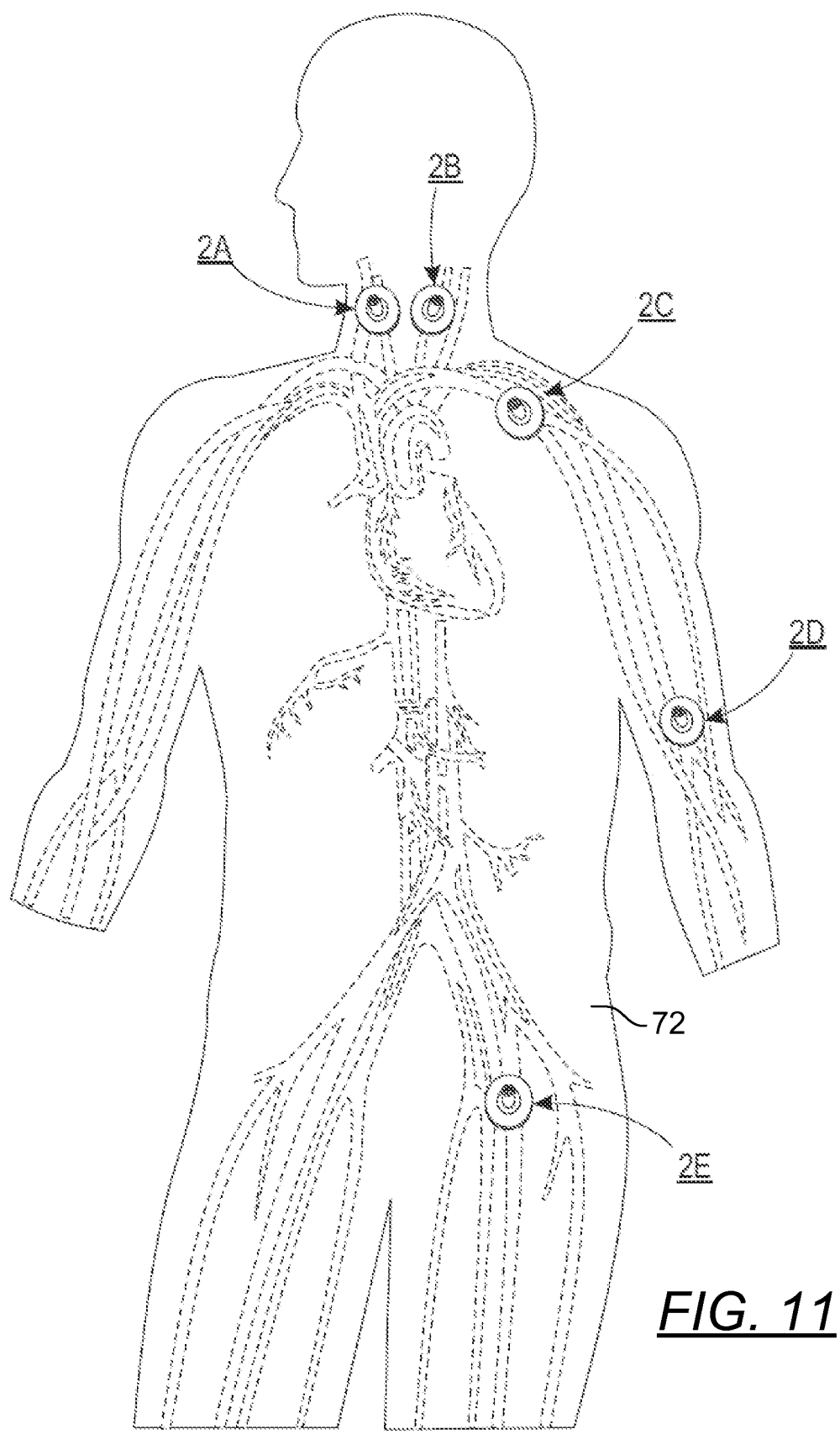
FIG. 11 is a diagram depicting exemplary locations where catheter ports may be used on a human.

FIGS. 10 and 11 are diagrams depicting exemplary locations where catheter ports may be used on a human. FIG. 10 depicts a Peripherally Inserted Central Catheter (PICC) administered through an entry point at a patient's arm. A PICC is inserted in a peripheral vein in the arm, such as the cephalic vein, basilic vein or brachial vein, and then advanced proximally toward the heart through increasingly larger veins, until the tip rests in the distal superior vena cava or cavoatrial junction. FIG. 11 depicts other access points to the central venous system. Catheter ports 2A, 2B are administered for access of catheters into to a large vein in the neck (internal jugular vein). Catheter port 2C is administered for access of catheters into the subclavian vein or axillary vein. Catheter port 2E is administered for access of catheters into the femoral vein in the groin. Although in conventional practices with catheters, extended periods of catheter access into the femoral vein in the groin is frowned upon as this area is typically moist and not hygienic. However, access through the groin presents a much lower health risk as compared to access through the internal jugular vein where catheter ports 2A and 2B are disposed. The present catheter port aids in lowering the risk of administering a catheter through the internal jugular vein by encouraging administration of a catheter through the groin instead although it can be used in with any central venous catheter.

Figure 12:
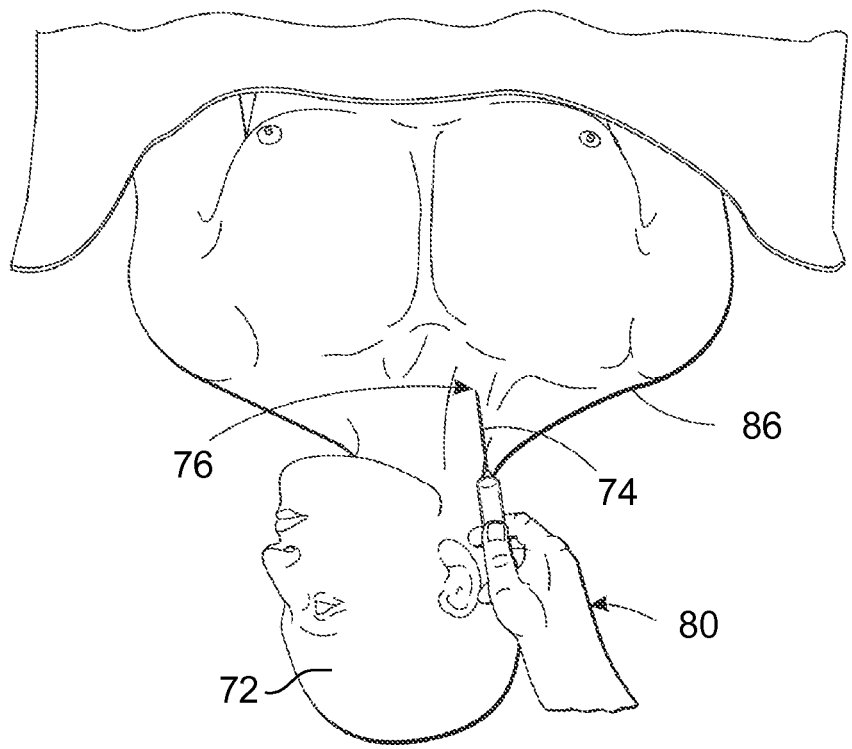
FIGS. 12-19 are diagrams depicting exemplary steps taken to administer a catheter port.
Figure 13:
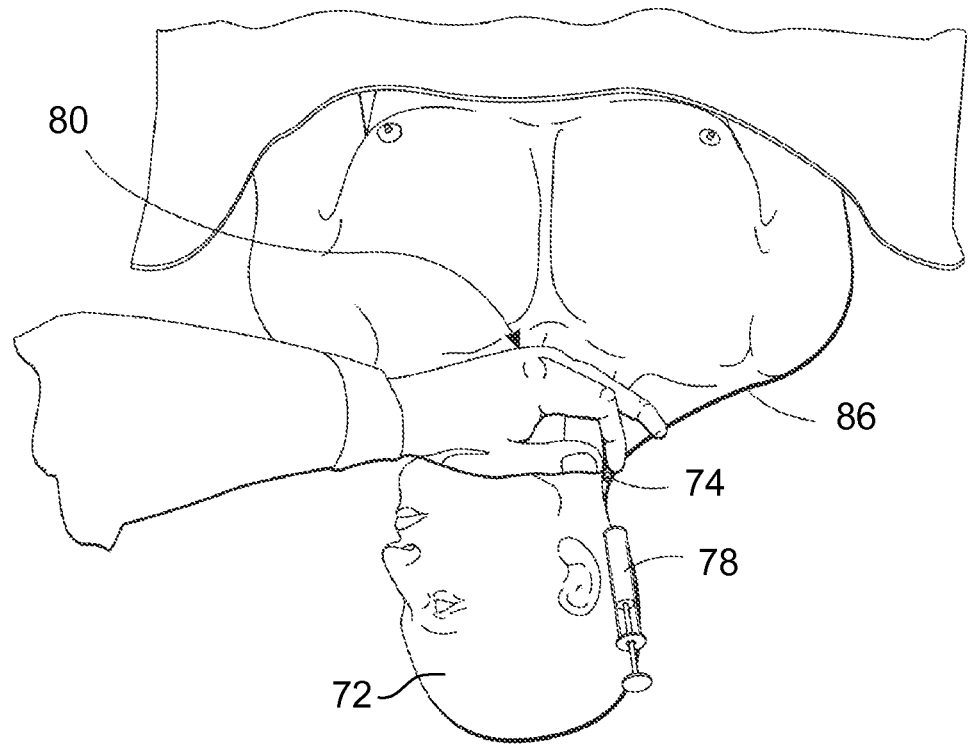
Figure 14:
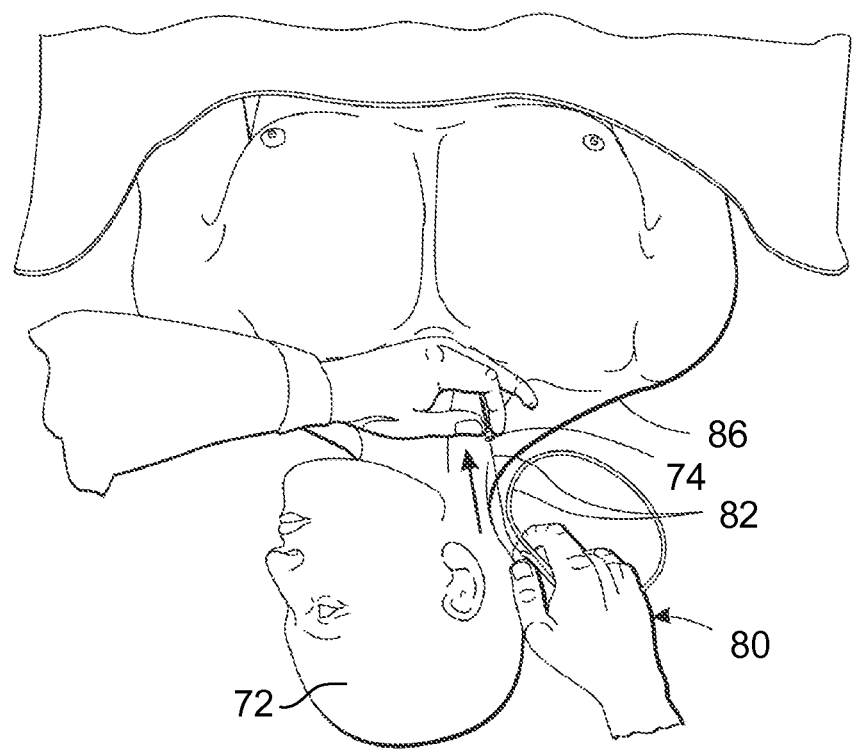
Figure 15:
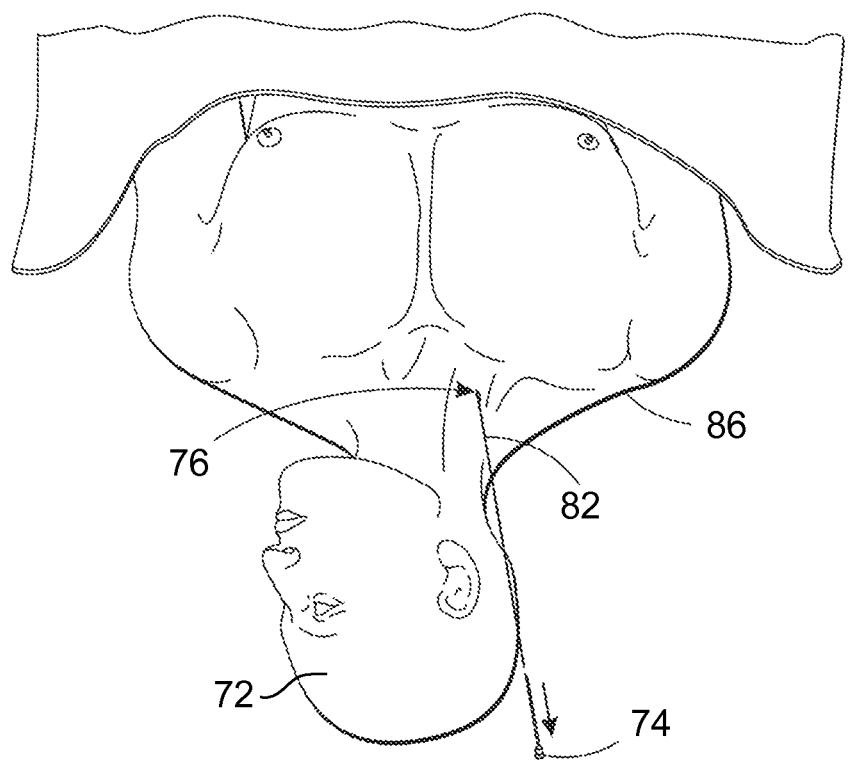
Figure 16:
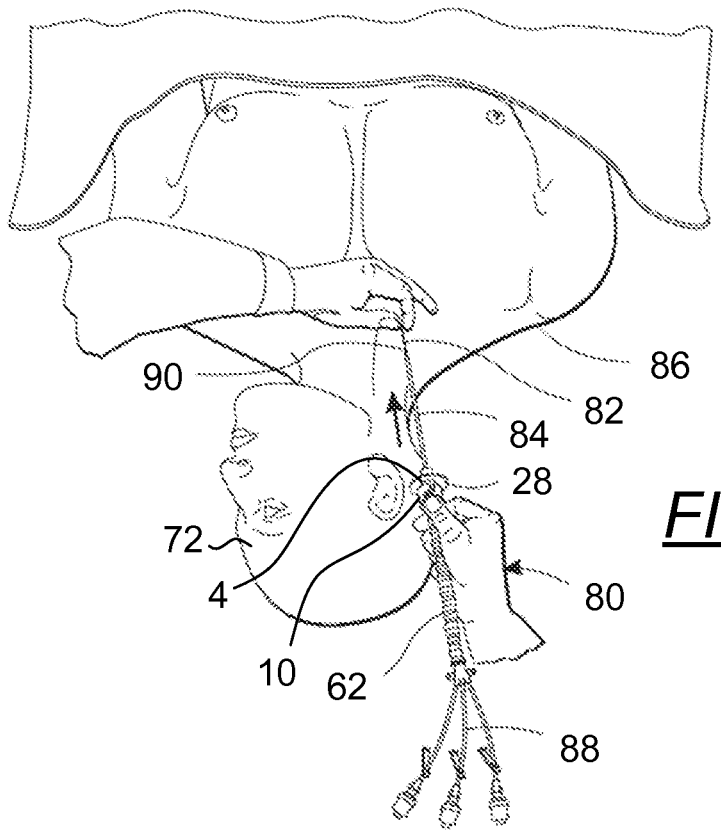
Figure 17:
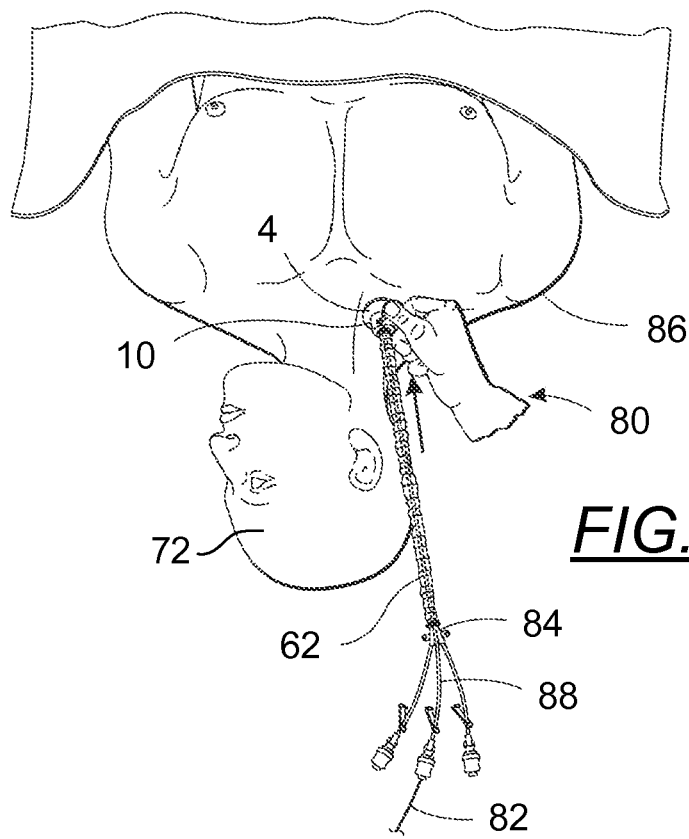
Figure 18:
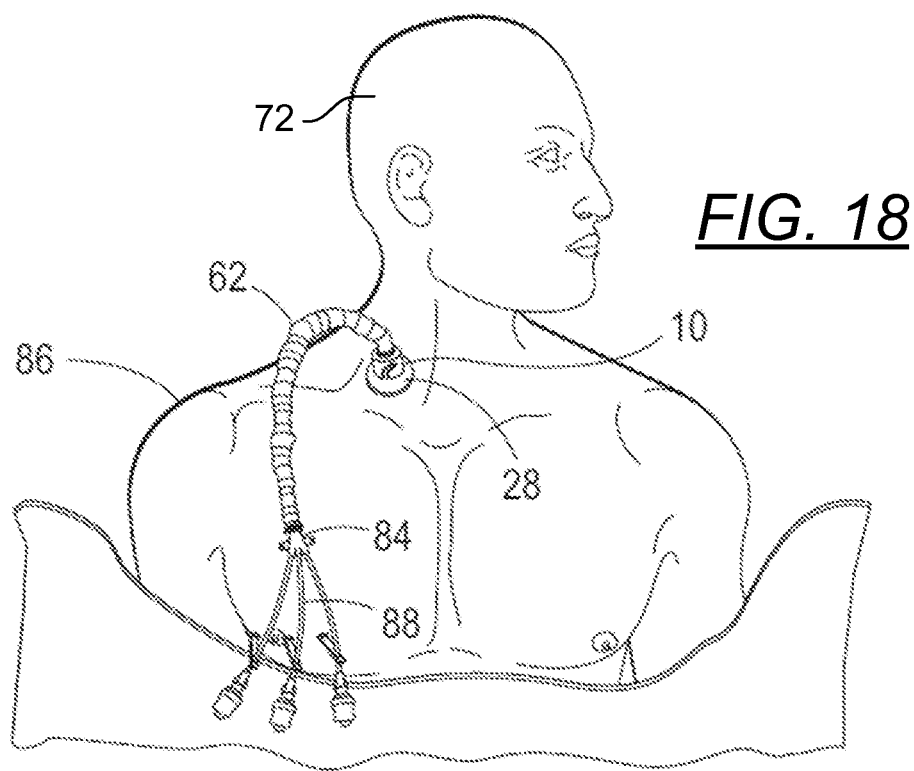
Figure 19:
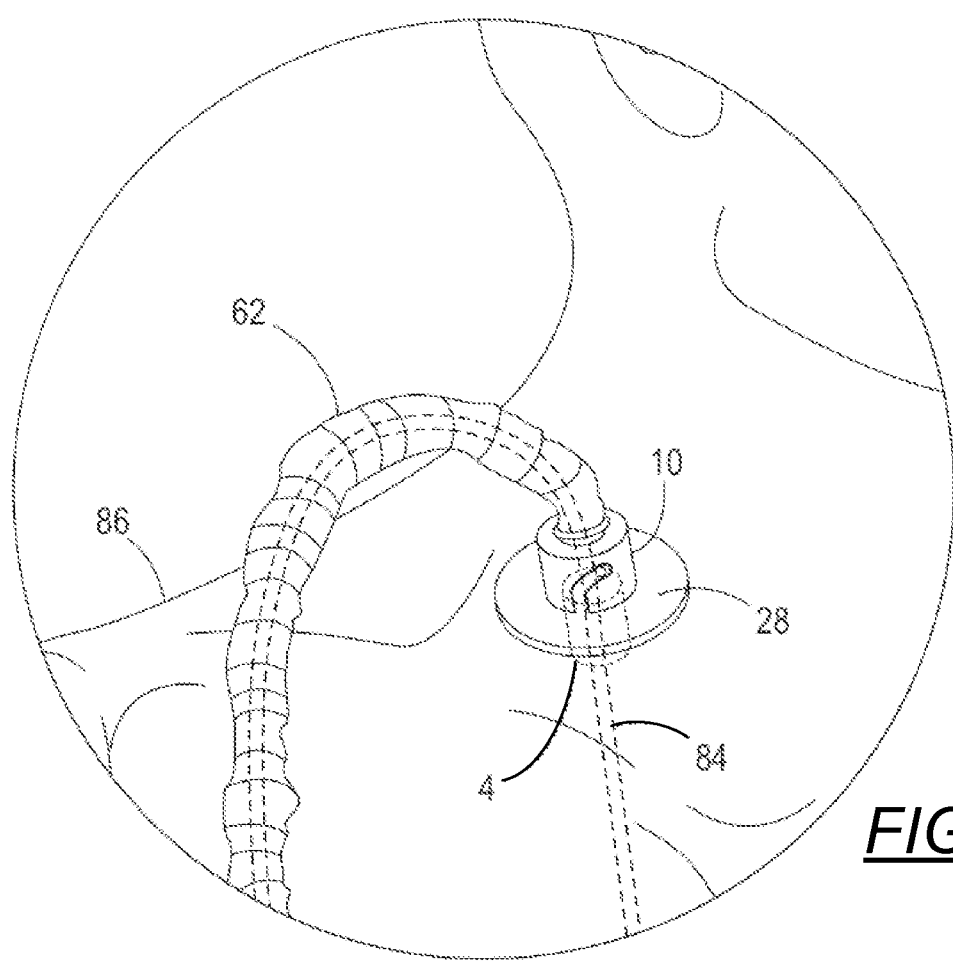

FIGS. 12-19 are diagrams depicting exemplary steps taken to administer a central venous catheter with a catheter port. In administering a catheter port, a sterile field is first created at the insertion or puncture site 76. A needle 74 is then placed through skin tissue into a body lumen, e.g., a vein until bleedback is achieved as shown in FIGS. 12-13. This is followed by introduction of a guidewire 82 through the skin and into the body lumen to a desired depth within the body lumen at its distal end as shown in FIGS. 14-15. The needle 74 is then exchanged for an introducer sheath with dilator, which are concentric tubes that are advanced over the guidewire 82 and into the body lumen. The needle 74 is removed by sliding the needle in a direction from the distal end of the guidewire 82 to the proximal end of the guidewire 82. The proximal end of the guidewire 82 is then inserted through a lumen of a dilator such that the dilator can be pulled in place to enlarge the passageway surrounding the needle 74. The dilator is then removed, and exchanged for a catheter. Prior to inserting a catheter in the patient's body, the catheter is inserted through a lumen of a present catheter port in the direction from the septum to the inner tube until the present catheter port is disposed roughly at the proximal end of the catheter and the guidewire 82 is removed. The catheter is then inserted in the patient's body through the insertion site 76 until its distal end is properly disposed. FIG. 16 depicts a catheter being inserted into the patient 72 with the aid of guidewire 82. FIG. 17 depicts a position of the catheter port having been seated in the surgical site. FIG. 18 depicts an administered catheter with a guidewire previously removed. FIG. 19 is a close-up view of an installed catheter port. Referring back to FIG. 16, a catheter port optionally coupled with a sleeve assembly is disposed over a multi-lumen catheter (a catheter having multiple dedicated catheter channels 88 via a single device) although a single channel catheter can also be used. The present catheter port is then pulled towards the insertion site 76 until the cushion becomes seated atop the skin or attached to the skin and the inner tube fully inserted in the patient's body/subcutaneous tissue. Therefore, it can be summarized that in administering a catheter port, the following steps shall be taken. First, a catheter port 2 is provided where the catheter port 2 includes a cushion 28 attached to a member 4, an inner tube 6 mounted to the member 4 and an aperture disposed in the member 4. A catheter is inserted through the catheter port 2 through the aperture of the member and the opening of the inner tube until the catheter port 2 is disposed at the proximal end of the catheter. The catheter is then inserted with its distal end first into the insertion site until the distal end has reached its intended depth or within the vein. The catheter port 2 is then pulled towards the patient until the cushion 28 has been placed with its bottom surface coming into contact with the patient's epidermis at the insertion site and the inner tube has extended into the patient's body about the site for guiding movement of a catheter 16 relative to the site and for preventing any portion of the catheter from ever contacting the patient's epidermis. The cushion 28 is adhered and secured to the patient's epidermis such that the cushion 28 surrounds the site through which the catheter is to be inserted. Upon installation of a catheter and a catheter port, no portion of the catheter will contact the patient's epidermis, thereby reducing the opportunity for infection due to contact with the patient's epidermis.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

I claim:

1. A catheter port adapted to be selectively secured topically to a patient's body about a site at which a catheter is to be inserted into said patient's body, said catheter port comprising:
   a cushion adapted to be secured to the patient's body about the site,
said cushion having a bottom surface arranged to face toward the patient's epidermis, an aperture through which the catheter is to be inserted and a top surface attached to a first end of a member; and
   an inner tube having a an inner diameter, a first end and a free second end, said inner tube mounted at said first end of said inner tube to said first end of said member, said free second end of said inner tube is adapted to only extend into the patient's body at and below the epidermis about the site for guiding movement of a catheter relative to the site and for preventing any portion of said catheter from ever contacting the patient's epidermis;
   an outer tube having an inner diameter, a proximal end, an intermediate portion and a distal end, said outer tube is configured to extend away from a second end of said member at said proximal end and said intermediate portion is configured to extend away from said second end of said member to said distal end, said outer tube distal end is arranged to be flexed relative to said outer tube proximal end and said intermediate portion comprises a bellows portion to accommodate such flexing, said intermediate portion is disposed between said outer tube distal end and said outer tube proximal end, wherein said second end of said member is oppposingly disposed from said first end of said member and an entirety of said inner diameter of said outer tube is larger than said inner diameter of said inner tube; and
   a septum mounted on said distal end of said outer tube, said septum is adapted to allow a catheter to be selectively inserted into, and removed from the patient's body through the site and maintain a gap between the catheter having a diameter smaller than said inner diameter of said outer tube to avoid contact between said outer tube and the catheter, whereby said catheter may be selectively inserted into, and removed from, the patient's body without ever contacting the patient's epidermis.

2. The catheter port as set forth in claim 1, wherein said septum comprises a plurality of slits radiating outwardly from a common point to allow penetration of the catheter.

3. The catheter port as set forth in claim 1, wherein at least a portion of said cushion is provided with an adhesive coating that is adapted to secure said cushion to the patent's epidermis.

4. The catheter port as set forth in claim 1, wherein at least a portion of said cushion is impregnated with an anti-microbial substance.

5. The catheter port as set forth in claim 1, wherein at least a portion of said cushion is impregnated with an antibiotic substance.

6. The catheter port as set forth in claim 1, wherein said cushion is formed of a foam material.

7. The catheter port as set forth in claim 1, further comprising at least one of an antibiotic substance and an anti-microbial substance acting between said bottom surface of said cushion and the patient's epidermis to provide a sterile field about the site.

8. The catheter port as set forth in claim 1, further comprising a sleeve assembly having a proximal end and a distal end, said sleeve assembly comprising a sleeve adapter disposed on said proximal end of said sleeve assembly, a support block disposed on said distal end of said sleeve assembly and a sleeve interposed between said proximal end of said sleeve assembly and said distal end of said sleeve assembly, wherein said sleeve adapter is configured to be adaptable to said distal end of said outer tube and the catheter may be inserted through and removed through said sleeve adapter, sleeve and support block and protected within said sleeve.

9. A method of inserting a catheter into a patient's body about a site, said method comprising the steps of:
   securing a cushion of a catheter port to the patient's body such that said cushion surrounds the site through which the catheter is to be inserted, said catheter port having a cushion, an inner tube and an outer tube, said cushion having a bottom surface, a top surface and an aperture, said bottom surface arranged to face toward the patient's epidermis, said aperture disposed in said cushion and said top surface attached to a first end of a member,
   said inner tube having an inner diameter, a first end and a free second end, said inner tube mounted at said first end of said inner tube to said first end of said member, said free second end of said inner tube that is adapted to only extend into the patient's body at and below the epidermis about the site,
   said outer tube having an inner diameter, a proximal end, an intermediate portion and a distal end, said outer tube is configured to extend away from a second end of said member and said intermediate portion is configured to extend away from said second end of said member to said distal end, said outer tube distal end is arranged to be flexed relative to said outer tube proximal end and said intermediate portion comprises a bellows portion to accommodate such flexing, said intermediate portion is disposed between said outer tube distal end and said outer tube proximal end, wherein said second end of said member is opposingly disposed from said first end of said member and an entirety of said inner diameter of said outer tube is larger than said inner diameter of said inner tube;

inserting said inner tube into the patient's body about the site for guiding movement of a catheter relative to the site and for preventing any portion of the catheter from ever contacting the patient's epidermis; and inserting the catheter through an opening of said outer tube and an opening of said inner tube into the patient's body such that no portion of the catheter ever contacts the patient's epidermis, thereby to reduce the opportunity for infection when inserting a catheter into the patient's body.

10. The method as set forth in claim 9, further comprising applying at least one of an antibiotic substance and an anti-microbial substance between a portion of said cushion and the patient's epidermis to provide a sterile field about the site.

11. The method as set forth in claim 9, wherein said cushion is formed of a foam material.

\* \* \* \* \*